United States Patent [19]

Malouvier et al.

[11] Patent Number: 5,107,860
[45] Date of Patent: Apr. 28, 1992

[54] METHOD AND APPARATUS OF ANALYZING THE FUNCTIONING OF THE LUNGS

[75] Inventors: Dominique Malouvier; Peter Müller, Georgenstrasse 126, 8000 München 40; Oscar Sebastiani, Klenzestrass 81, 8000 München 5, all of München, Fed. Rep. of Germany

[73] Assignees: Peter Muller; Oscar Sebastiani, both of Munich, Fed. Rep. of Germany

[21] Appl. No.: 581,159

[22] Filed: Sep. 7, 1990

Related U.S. Application Data

[63] Continuation of Ser. No. 258,110, Oct. 13, 1988, abandoned, which is a continuation of Ser. No. 893,854, Aug. 6, 1986, abandoned.

[30] Foreign Application Priority Data

Aug. 16, 1985 [DE] Fed. Rep. of Germany ....... 3529367

[51] Int. Cl.⁵ .................................................. A61B 5/08
[52] U.S. Cl. ................................. 128/720; 128/204.17
[58] Field of Search ............ 128/716, 720, 725, 204.17

[56] References Cited

U.S. PATENT DOCUMENTS

| | | | |
|---|---|---|---|
| 3,621,833 | 11/1971 | Crane | 128/720 |
| 3,626,755 | 12/1971 | Rudolph | 73/861.52 |
| 3,713,436 | 1/1973 | Hardway, Jr. | 128/720 |
| 4,051,843 | 10/1977 | Franetzki | 128/720 |
| 4,122,842 | 10/1978 | Pikul | 128/725 |
| 4,355,636 | 10/1982 | Oetjen et al. | 128/204.17 |

*Primary Examiner*—Randy C. Shay
*Attorney, Agent, or Firm*—Townsend and Townsend

[57] ABSTRACT

A method of measuring the real flow resistance of the lung function is described in which the function parameters are determined from absolute pressure and pressure difference measurements independently of a defined termination resistance.

9 Claims, 1 Drawing Sheet

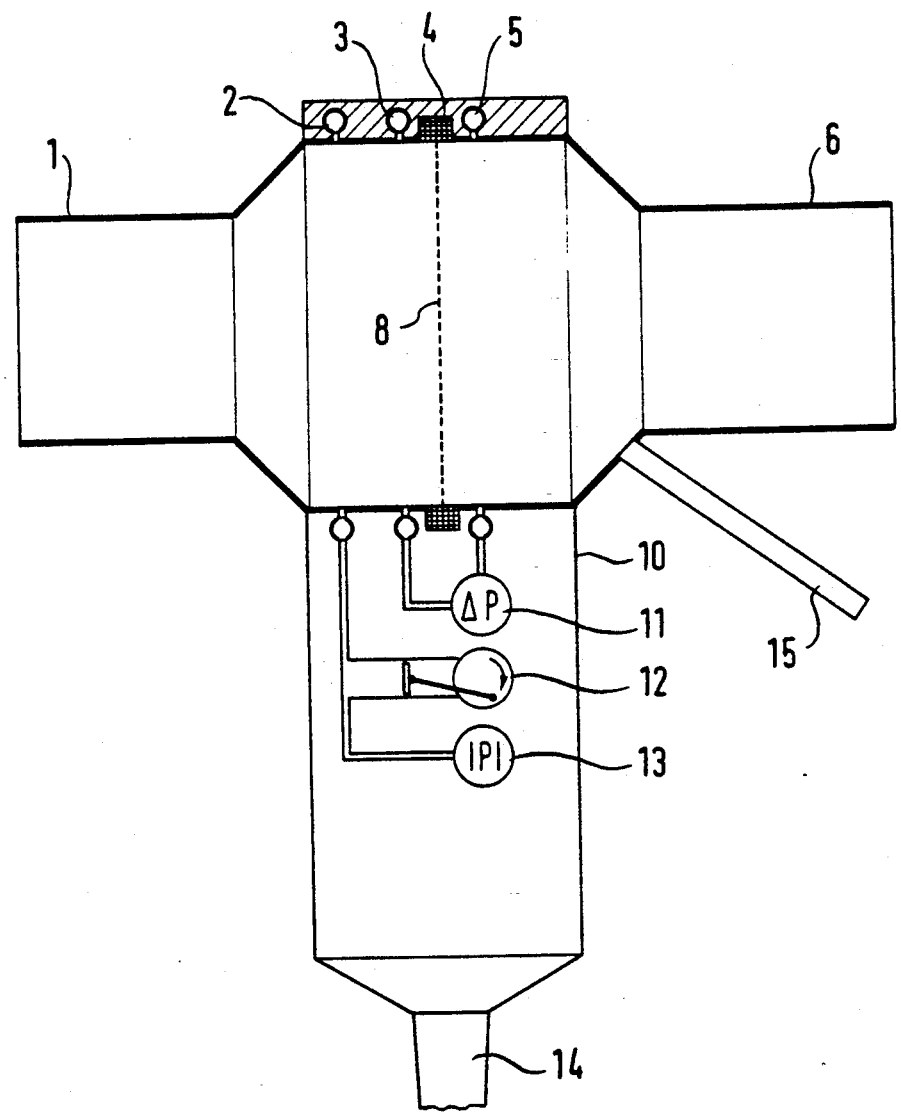

METHOD AND APPARATUS OF ANALYZING THE FUNCTIONING OF THE LUNGS

This application is a continuation of Ser. No. 07/258,110, filed Oct. 13, 1988, now abandoned, which is a continuation of Ser. No. 06/893,854, filed Aug. 6, 1986, now abandoned.

BACKGROUND OF THE INVENTION

The invention relates to a method for investigating the functioning of the lungs of a subject, and more particularly to measuring the real flow respiratory resistance of breathing passages.

Apparatuses for analyzing the functioning of the lungs serve for the early or timely recognition of obstructive diseases of the lungs, and also for the recognition of restrictive respiratory disturbances. They also make it possible to carry out pulmonary provocation investigations and tests for bronchialitis.

It is known within the context of lung function analysis to determine as respiratory parameters the respiratory volumes, the air flow and the flow resistance. The respiratory volume represents a static respiratory parameter, the air flow a dynamic respiratory parameter and the flow resistance the resistance of the breathing passages, whereby the pressure difference between the alveoli and the environmental air which has to be overcome corresponds to the flow resistance of the breathing passages.

The determination of the respiratory volumes and of the air flow takes place in known manner either in closed or half-open systems, or in open systems. In the context of the present invention it is the so-called open system which is in particular of significance, in which the quantity of air flowing is detected in an open tube and the respiratory volumes are deduced therefrom.

The resistance of the respiratory passages is determined in the context of the present invention in accordance with the oscillation method in which small oscillations are impressed on the respiratory flow of the patient. Furthermore, the method of frequency modulated oscillation is of significance in the context of the invention. By means of this method the resonant frequency of the respiratory passages of the subject can be deduced by frequency modulation of the oscillation. In this connection it is of advantage that the resistance measured at the resonant frequency is identical with the real flow resistance of the respiratory passages, because other resistances such as inertia and extensibility of the lungs cancel out.

The object of the present invention is to provide a method and an apparatus for the diagnosis of the lung function which operates extremely reliably and with high accuracy, which enables the determination of all the parameters of interest, which can be realized in compact form, which ensures simple operation and which meets the highest requirements from the point of view of hygiene.

It is important for the solution of this problem that one operates, in accordance with the invention, according to the so-called oscillation method in conjunction with a differential pressure measurement and an absolute pressure measurement, and that one simultaneously uses a branch principle which makes it possible to operate without a specific precisely defined terminal resistance. By measuring the differential pressure, i.e. the difference of the pressures on the two sides of a fine-meshed wire net arranged in a measuring tube, by measuring the absolute pressure in the subject side of the measuring tube, and also by feeding a pulsed partial flow into the measuring tube at least on the side of the fine-meshed wire net remote from the subject, whilst simultaneously leading off the remainder of the partial flow via a hose section of non-critical length which continues the measuring tube, one obtains surprisingly high measurement accuracies with the simplest manner of operation which is most favorable for the subject.

A pulsed air supply is preferably used with a steady flow component such that a part of the pulsed air which is supplied continuously emerges via the hose section which belongs to the branch, which ensures that the subject breathes in exclusively freshly supplied air and that the sucking back of consumed air does not occur. This is of significance because in this way it is ensured that falsification of the measured values by re-breathed air can be avoided.

Furthermore, it is a significant advantage that constant measurement conditions are obtained, in particular with regard to temperature and humidity which again contributes to an increase of the accuracy of the finally obtained measured values.

Having regard to the attainment of a measurement accuracy which is as high as possible, it is furthermore of important significance for the invention that an element with a very low mass is used as the fine-meshed grid or net which can be rapidly controlled temperature-wise by a small supply of energy in order to prevent condensation effects on the grid or net. The grid or net is preferably inductively heated with the temperature being regulated in dependence on the flow, i.e. the quantity of air and the direction of the flow as well as the temperatures of the flows in the respective directions are taken into-account in the computer controlled regulation in accordance with the invention. The mean temperature of the net or grid is moreover directly detected via a sensor.

In its practical realization a system in accordance with the invention consists of a basic apparatus with an integrated printer, an input unit which is in particular constructed as a foil keyboard, a measuring head with pneumotachographs for measuring volumes and flow, and also a pressure pick-up part for measuring the resistances and a video screen for presenting data and graphs. The flow curve and the volume curve are preferably plotted relative to the time axis and the flow curve relative to the volume is preferably also shown. Moreover, the actual air pressure and also the room temperature are independently deduced and made use of during the running of the program.

It is possible, as a result of the measured values that are obtained to derive all the important lung function parameters and indeed in particular the vital capacity, the inspiratory reserve volume, the exploratory reserve volume, the breathing volume, the formed vital capacity, the absolute second capacity and also the relative second capacity. The real actual values that are deduced can be set into relation with the stored normal values which represents a significant simplification so far as the evaluation is concerned.

Both the inspiratory and also the exspiratory flow volume curves can be determined by means of a microprocessor controlled computer from the volumes measured in the pneumotachograph in relation to the time axis, with the maximum exspiratory flow, the maximum inspiratory flow and also the forced exspiratory flow and further relative values being additionally derivable.

Further special features of the invention will be described in the following with reference to the drawing.

BRIEF DESCRIPTION OF THE DRAWING

The FIG. shows a schematic representation of an apparatus used with the method of the present invention.

DETAILED DESCRIPTION OF THE PREFERRED EMBODIMENT

The measuring head 2A which serves to determine the function parameters includes of a tube 3A which is preferably manufactured in plastic with a diameter of approximately 25 to 30 mm which is broadened at its central region, 5A which accommodates the measuring apparatus, to approximately 50 mm and a handle 10.

A mouth piece 1A which represents a disposable article is pushed onto the subject side end 1 of the tube 3A. During the respiratory measurement the subject must hold the mouth piece in the mouth.

A tube or hose 6A can be pushed onto the opposite other end 6 of the tube 3A during breathing resistance measurement in order to exert a branch function with regard to a pulsed air stream with steady flow component supplied via a connection 15.

The entire measuring tube with the inbuilt elements can be plugged onto a handle 10. This connection is made easily releasable so that problem free removal and serialization of the measuring tube 3A can be carried out.

A fine-meshed wire net 8 is mounted at the center of the tube 3A and extends over the entire cross-section of the tube. The pressure difference produced by the air flow is measured at this wire net. The wire net 8 preferably consists of a non-rusting metal and has a mesh width of 20 $\mu$ with a square mesh shape. This corresponds to 1270 filaments per inch.

The measurement of the pressure drop at the wire net 8 takes place by a pressure pick-up 11, in particular a piezopressure pick-up with an integrated amplifier. This pressure pick-up is connected with the measuring tube 3A via very short connection lines 77 which lie fully protected in the handle 10 and via ring channels 3, 5 which are formed in the measuring tube on both sides of the wire net 8. A special feature of these ring channels 3, 5 lies in the fact that they communicate with the inner space of the measuring tube 32 via bores (not shown) distributed around the periphery, so that in this way a mean value is formed of the pressure prevailing on the two sides of the wire net 8. In this way inhomogeneity of the air flow, considered over the full cross-section, is excluded.

As the air breathed out by the subject is at body temperature and has a relative humidity of 100% care must be taken to prevent the formation of a deposit of moisture on the surface of the wire net 8. This fine-meshed wire net 8 must therefore be heated at least to body temperature in order to prevent this condensation. Condensation which forms would namely increase the air resistance of the wire net and lead to considerable measuring errors, moreover the danger would exist that germs from the breathed air would rapidly multiply in the moist environment.

In accordance with the invention the required heating of the fine meshed wire net 8 which has a very low mass takes place inductively, and indeed through a coil 4 which is embedded in the measuring tube and surrounds the wire net 8 in its plane.

As a result of the low mass of the wire net 8 a very rapid temperature-wise control of this wire net can take place through a small supply of energy. The regulation of the temperature takes place analogously to the flow, i.e. the air quantity and direction of the air flow are taken into account in the same manner as the temperature of the flow in the respective directions is taken into account. Moreover, the mean temperature of the grid is directly measured via a sensor 50. The temperature of the air flow must essentially only be distinguished from the point of view of its direction, because the temperature of the air in the room is automatically detected, and this represents the temperature of the air flow in the one direction, whereas the air flow in the other direction, which corresponds to the exhaling of the subject, generally amounts to approximately 37° C. corresponding to the body temperature. When the corresponding measured values are available the supply of energy to the wire net 8 can be exactly controlled without problems by a suitable program which has extremely advantageous effects with regard to the achievable measurement accuracy. Coil 4, connected to computing unit 100 through leads 60, 61, is used for inductive heating of wire net 8. Lead 90 connects temperature sensor 50 to computing unit 100; unit 100 regulates and maintains the temperature of wire net 8.

In the same manner as for the detection of the differential pressure, it is also of important advantage for the absolute pressure measurement which takes place at the subject side that the respective pressure sensor is accommodated in the handle 10, so that very short connection lines can be used which are not subject to any danger of kinking and can thus also not falsify the measurement result in any way. Absolute and differential pressure measurements are provided computing unit 100 through differential sensor 100 and leads 77. The generation of an oscillating air flow is necessary for the respiratory resistance measurement. For this purpose a membrane pump 12 is provided in the handle 10, in accordance with an embodiment of the invention, and generates an oscillating air flow which is directed via a ring channel 2 in the measuring tube 3A into the mouth and pharynx of the subject. The oscillation pressure in the mouth is measured by a piezo device 13 for measuring the absolute pressure. Piezo device 13 is connected to computing unit 100 through a lead 75. This device 13 is likewise accommodated in the handle 10. Leads 60, 61 75, 77 and 90 are routed through a spiral cable 14, which is preferably of flexible construction, from measuring head 28 to computing unit 100.

The feeding in of the oscillating air stream which is generated by the pump 12 can also take place via a connection 15 which is illustrated purely schematically. The pressure measurement via the absolute pressure sensor 13 remains unchanged in this embodiment.

The pump 72 used to supply the oscillating air stream is preferably so constructed that it has an easily opening suction valve (not shown) which precludes reverse sucking out of the hose 6A by the pump itself from occurring, because the resistance of the corresponding hose or of the connection line is too high.

It is important for the invention that the pulsed air supply, the pulsation frequency of which preferably lies in the range from 2 to 20 Hertz takes place in such a way, and with a steady flow component, such that a part of the air supplied continuously emerges via the end 6 of the measuring head 2A opposite to the subject. It is ensured in this wa the patient inhales exclusively freshly supplied air and does not rebreathe used air. The discharging of a part of the supply of air takes place in this arrangement in the manner of a branch, with the branch conditions being predetermined by the choice of the termination piece, or by the provision of a connection hose 6A. The length of the hose 6A is however completely non-critical. This is a consequence of the fact that the measurement values are obtained via an absolute pressure measurement and a differential pressure measurement, independently of a particular terminal resistance.

By measuring with frequency modulated oscillations the resonant frequency of the respiratory passages of the subject can be determined. Because in this case the measured resistance is identical to the real flow resistance of the respiratory passages, a particularly high measurement accuracy results, and indeed in particular with high degree obstructions.

We claim:

1. A method of determining the real flow resistance of the lungs of a subject comprising the steps of:
    (a) providing a subject with a mouthpiece for inhaling and exhaling, said mouthpiece being connected to a measuring head through a flow passage, the flow passage including a fine meshed metallic grid disposed therein;
    (b) supplying an air stream with a steady flow component to said flow passage for said subject to breathe, so that a part of the air stream which is supplied continuously passes into the atmosphere via a section of hose of non-critical length forming a terminal resistance, said hose being connected to said flow passage in said measuring head on the opposite side of said metallic grid from said mouthpiece, which enables that the subject breathes in exclusively freshly supplied air and that sucking back of consumed air does not occur;
    (c) impressing small frequency modulated oscillations on the respiratory flow of the patient;
    (d) regulating the temperature of said metallic grid in dependence on the flow by measuring the temperature of said metallic grid and by supplying energy to it to heat it to a temperature sufficient to prevent condensation thereon;
    (e) measuring the absolute pressure on the mouthpiece side of said metallic grid;
    (f) measuring the differential pressure across said metallic grid; and
    (g) calculating the real flow resistance of the lung from said absolute pressure measurement and said differential pressure measurement at the resonant frequency of the subject's respiratory passages.

2. A method in accordance with claim 1, wherein the step of impressing small frequency oscillations on the respiratory flow of the patient is effected by making said air stream with a steady flow component a pulsed air stream with a steady flow component.

3. The method for determining flow resistance of claim 1 wherein said metallic grid is heated to approximately 40° C.

4. A method of determining the real flow resistance of the lungs of a subject comprising the steps of:
    (a) providing a subject with a mouthpiece for inhaling and exhaling, said mouthpiece being connected to a measuring head through a flow passage, the flow passage including a fine meshed metallic grid disposed therein;
    (b) supplying an air stream with a steady flow component to said flow passage for said subject to breathe, so that a part of the air stream which is supplied continuously passes into the atmosphere via a section of hose of non-critical length forming a terminal resistance, said hose being connected to said flow passage in said measuring head on the opposite side of said metallic grid from said mouthpiece, which enables that the subject breathes in exclusively freshly supplied air and that sucking back of consumed air does not occur;
    (c) impressing small frequency modulated oscillations on the respiratory flow of the patient;
    (d) regulating the temperature of said metallic grid by measuring the temperature of said metallic grid and supplying energy to it to heat it to at least a body temperature of said subject sufficient to prevent condensation thereon;
    (e) measuring the absolute pressure on the mouthpiece side of said metallic grid;
    (f) measuring the differential pressure across said metallic grid;
    (g) calculating the real flow resistance of the lung from said absolute pressure measurement and said differential pressure measurement at the resonant frequency of the subject's respiratory passages.

5. A method for determining real flow resistance in accordance with claim 4, wherein the step of impressing small frequency oscillations on the respiratory flow of the patient is effected by making said air stream with a steady flow component a pulsed air stream with a steady flow component.

6. A method of determining the real flow resistance of the lungs of a subject comprising the steps of:
    (a) providing a subject with a mouthpiece for inhaling and exhaling, said mouthpiece being connected to a measuring head through a flow passage, the flow passage including a fine meshed metallic grid disposed therein;
    (b) supplying an air stream with a steady flow component to said flow passage for said subject to breathe, so that a part of the air stream which is supplied continuously passes into the atmosphere via a section of hose of non-critical length forming a terminal resistance, said hose being connected to said flow passage in said measuring head on the opposite side of said metallic grid from said mouthpiece, which enables that the subject breathes in exclusively freshly supplied air and that sucking back of consumed air does not occur;
    (c) impressing small frequency modulated oscillations on the respiratory flow of the patient;
    (d) regulating the temperature of said metallic grid by measuring the temperature of said metallic grid and inductively heating said metallic grid to a temperature sufficient to prevent condensation thereon;
    (e) measuring the absolute pressure on the mouthpiece side of said metallic grid;
    (f) measuring the differential pressure across said metallic grid;
    (g) calculating the real flow resistance of the lung from said absolute pressure measurement and said differential pressure measurement at the resonant frequency of the subject's respiratory passages.

7. The method for determining real flow resistance in accordance with claim 6, wherein the step of regulating the temperature of said metallic grid comprises inductively heating said metallic grid to at least a body temperature of said subject.

8. The method for determining real flow resistance of claim 6 wherein said metallic grid is heated to approximately 40° C.

9. A method for determining real flow resistance in accordance with claim 6, wherein the step of impressing small frequency oscillations on the respiratory flow of the patient is effected by making said air stream with a steady flow component a pulsed air stream with a steady flow component.

* * * * *

UNITED STATES PATENT AND TRADEMARK OFFICE
CERTIFICATE OF CORRECTION

PATENT NO. : 5,107,860
DATED : April 28, 1992
INVENTOR(S) : Malouvier, et al.

It is certified that error appears in the above-indentified patent and that said Letters Patent is hereby corrected as shown below:

On the title page and column 1, line 1:
Kindly delete the words "AND APPARATUS" from the title of the patent.

In col. 1, line 2, kindly delete "AND APPARATUS" from the title.

In col. 2, line 37, after the word "into", kindly delete the hyphen.

In col. 3, line 49, kindly delete "32" and insert therefor --3A--.

In col. 5, line 2, kindly delete "wa" and insert therefor --way--.

In col. 6, line 24, kindly insert after the word "grid;", --and--.

In col. 6, line 62, kindly insert after the word "grid;", --and--.

Signed and Sealed this

Fifteenth Day of November, 1994

Attest:

BRUCE LEHMAN

Attesting Officer     Commissioner of Patents and Trademarks